United States Patent
Makower et al.

(10) Patent No.: US 9,381,270 B2
(45) Date of Patent: *Jul. 5, 2016

(54) MUCOSAL TISSUE DRESSING AND METHOD OF USE

(71) Applicant: Acclarent, Inc., Menlo Park, CA (US)

(72) Inventors: Joshua Makower, Los Altos, CA (US); John Y. Chang, Los Altos, CA (US); Ketan P. Muni, San Jose, CA (US); Wenda Carlyle, Newtown, CT (US); Howard Levine, Longboat Key, FL (US); William M. Facteau, Atherton, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,619

(22) Filed: Jun. 18, 2014

(65) Prior Publication Data

US 2014/0350526 A1 Nov. 27, 2014

Related U.S. Application Data

(63) Continuation of application No. 12/341,315, filed on Dec. 22, 2008, now Pat. No. 8,795,713.

(60) Provisional application No. 61/052,413, filed on May 12, 2008, provisional application No. 61/017,976, filed on Dec. 31, 2007.

(51) Int. Cl.
| | | |
|---|---|---|
| A61F 13/00 | (2006.01) | |
| A61F 2/00 | (2006.01) | |
| A61L 26/00 | (2006.01) | |
| A61L 15/42 | (2006.01) | |
| A61L 15/44 | (2006.01) | |
| A61L 15/58 | (2006.01) | |
| A61L 15/64 | (2006.01) | |
| A61K 9/00 | (2006.01) | |

(52) U.S. Cl.
CPC ....... *A61L 26/0023* (2013.01); *A61F 13/00017* (2013.01); *A61L 15/42* (2013.01); *A61L 15/44* (2013.01); *A61L 15/58* (2013.01); *A61L 15/64* (2013.01); *A61L 26/009* (2013.01); *A61L 26/0061* (2013.01); *A61L 26/0066* (2013.01); *A61F 2013/00357* (2013.01); *A61K 9/006* (2013.01); *A61L 2300/402* (2013.01); *A61L 2300/406* (2013.01); *A61L 2300/41* (2013.01); *A61L 2300/608* (2013.01); *Y10T 156/10* (2015.01)

(58) Field of Classification Search
None
See application file for complete search history.

(56) References Cited

U.S. PATENT DOCUMENTS

| | | | |
|---|---|---|---|
| 3,996,934 A | 12/1976 | Zaffaroni | |
| 4,614,787 A * | 9/1986 | Szycher et al. | 528/75 |
| 5,137,729 A | 8/1992 | Kuroya et al. | |
| 5,456,745 A | 10/1995 | Roreger et al. | |
| 5,605,696 A | 2/1997 | Eury et al. | |
| 5,882,324 A | 3/1999 | Baranowski | |
| 6,051,249 A | 4/2000 | Samuelson | |
| 6,635,272 B2 | 10/2003 | Leaderman | |
| 6,803,420 B2 | 10/2004 | Cleary et al. | |
| 7,005,556 B1 | 2/2006 | Becker et al. | |
| 7,270,651 B2 | 9/2007 | Adams et al. | |
| 8,088,095 B2 | 1/2012 | Hissong et al. | |
| 8,795,713 B2 | 8/2014 | Makower et al. | |
| 2003/0135174 A1 | 7/2003 | Benecke et al. | |
| 2005/0048102 A1 | 3/2005 | Tapolsky et al. | |
| 2007/0123492 A1 | 5/2007 | Prestwich et al. | |
| 2008/0195037 A1* | 8/2008 | Hissong et al. | 604/48 |
| 2009/0089087 A1 | 4/2009 | Kotecki et al. | |
| 2010/0152730 A1 | 6/2010 | Makower et al. | |

FOREIGN PATENT DOCUMENTS

| | | |
|---|---|---|
| CN | 101018519 | 7/2005 |
| JP | H02-237916 | 9/1990 |
| JP | 2001-163745 | 6/2001 |
| JP | 2001-508037 | 6/2001 |
| JP | 2001-508038 | 6/2001 |
| JP | 2002-512950 | 5/2002 |
| JP | 2007-502823 | 2/2007 |
| WO | WO 2005027852 | 3/2005 |

OTHER PUBLICATIONS

Australian Patent Examination Report dated Apr. 19, 2013 for Application No. AU 2008346830.
Australian Patent Examination Report dated Mar. 28, 2014 for Application No. AU 2008346830.
Chinese Office Action dated Oct. 13, 2012 for Application No. CN 200880127420.9.
Chinese Search Report for Application No. CN 200880127420.9.
(Continued)

*Primary Examiner* — Susan Tran
(74) *Attorney, Agent, or Firm* — Frost Brown Todd LLC

(57) ABSTRACT

A method and apparatus for reducing or eliminating pain after surgical procedures related to mucosal tissue, including tonsillectomy, adenoidectomy, or other pharyngeal operations. Certain embodiments provide a biodegradable film or covering that serves as a mechanical barrier to reduce pain caused, for example, by friction between solid food and healing tissue in the first few days after surgery. Some embodiments may include one or more therapeutic substances for locally reducing pain, facilitating healing and/or otherwise treating mucosal tissue at or near a tonsil bed.

19 Claims, 10 Drawing Sheets

(56) References Cited

OTHER PUBLICATIONS

European Communication dated Oct. 15, 2012 for Application No. EP 08870494.5.
International Search Report dated Mar. 2, 2010 for Application No. PCT/US2008/087920.
Japanese Notice of Rejection dated Jun. 18, 2013 for Application No. JP 2010-540822.
Mexican Examination Report dated Mar. 5, 2014 for Application No. MX/a/2010/007282.
Russian Office Action for Application No. RU 2007105308.
Canadian Examination Report dated Feb. 13, 2015 for Application No. CA 2,711,174, 4 pages.
Canadian Examination Report dated Sep. 29, 2015 for Application No. CA 2,711,174, 4 pages.
Chinese Office Action dated Nov. 13, 2012 for Application No. CN 200880127420.9, 11 pages.
Chinese Office Action dated Jul. 18, 2013 for Application No. CN 20080127420.9, 12 pages.
European Communication dated Jan. 23, 2012 for Application No. EP 08870494.5, 5 pages.
International Preliminary Report on Patentability dated Jul. 6, 2010 For Application No. PCT/US2008/087920, 7 pages.
Mexican Examination Report dated Sep. 19, 2013 for Application No. MX/a/2010/007282, 2 pages.
Mexican Examination Report dated May 23, 2014 for Application No. MX/a/2010/007282, 2 pages.

* cited by examiner

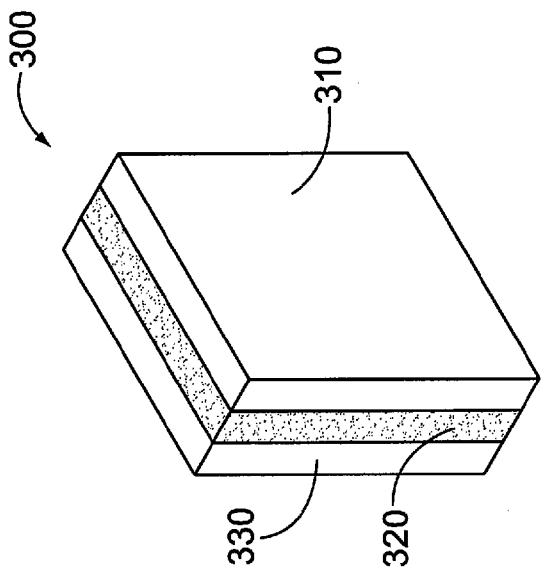
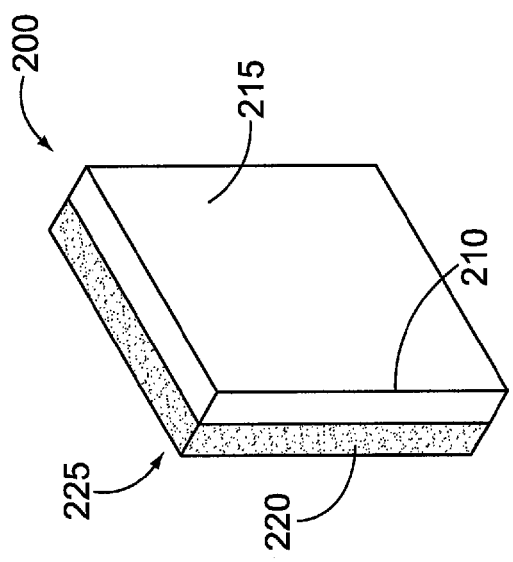
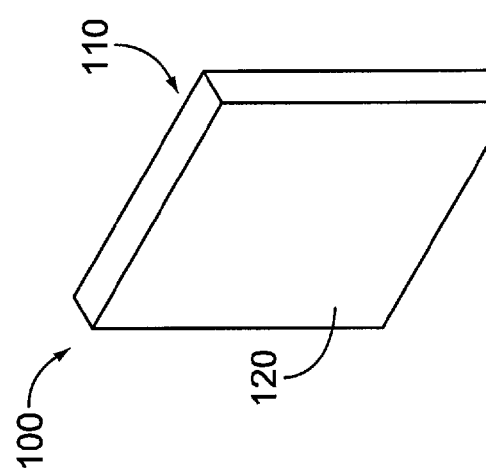

MUCOSAL TISSUE DRESSING AND METHOD OF USE

CROSS-REFERENCE TO RELATED APPLICATIONS

This application is a continuation of U.S. patent application Ser. No. 12/341,315, filed Dec. 22, 2008, now U.S. Pat. No. 8,795,713, issued on Aug. 5, 2014, which claims the benefit of U.S. Provisional Application No. 61/017,976, filed Dec. 31, 2007, and U.S. Provisional Application No. 61/052,413, filed May 12, 2008, all of which are herein incorporated by reference in their entirety.

BACKGROUND OF THE INVENTION

Tonsillectomy and adenoidectomy are two of the most common surgical procedures performed on children. Both tonsillectomy and adenoidectomy are associated with considerable post-operative pain that may often last as long as two weeks. Due to this post-operative pain, which is most severe when trying to swallow food, children typically cannot eat solid food for at least two days after surgery and often for as long as six days after surgery. In addition to post-operative pain, children also commonly suffer from post-operative bleeding, nausea, and/or bad breath after tonsillectomy/adenoidectomy. Although tonsillectomy and adenoidectomy are performed less commonly on adults, the procedures cause similar post-surgical pain and discomfort in adult patients.

Generally, surgical procedures on mucosal tissue, such as tonsillectomy and adenoidectomy, present several post-operative challenges. Mucosal tissue is typically very delicate and difficult to bandage. Mucosal tissue often must stay wet to heal and to perform its intended function. Damaged mucosal tissue can produce significant patient discomfort.

A number of tonsillectomy/adenoidectomy procedures have been developed in an attempt to reduce the post-operative pain and discomfort caused by the procedure. For example, the Coblation Tonsillectomy procedure developed by Arthrocare Corporation (Austin, Tex.) was developed as a "less invasive," and thus less painful, tonsillectomy method. However, even using the Coblation Tonsillectomy procedure or other less invasive procedures, post-operative pain and bleeding are still significant for many children and adult patients, often preventing them from eating food for days after their surgeries. To date, no satisfactory post-operative treatments have been developed to alleviate this pain and to allow patients to comfortably eat after tonsillectomy and adenoidectomy procedures.

Therefore, a need exists for a post-surgical treatment that would help children and adult patients recover from tonsillectomy and adenoidectomy. Ideally, such a treatment would act as a barrier to protect mucosal tissue at and around the surgical site to make it easier and less painful for a patient to swallow. Ideally, the barrier would adhere to mucosal tissue even with the abrasive forces of swallowing and, in addition to reducing pain, would also reduce bleeding. At least some of these objectives will be met by various embodiments of the present invention.

In addition to post-tonsillectomy/adenoidectomy treatment, there are many other treatments in the ear, nose, throat or mouth that could be performed or enhanced with a mucosal tissue dressing. For example, it would be desirable to have a mucosal tissue dressing that could adhere to tissue and deliver one or more therapeutic substances to a desired area in the ear, nose, throat or mouth. It would also be beneficial to have a dressing for stopping a cerebrospinal fluid leak, reducing blood loss from an incision, acting as a bolster or support to a piece of tissue and/or the like. In any of these contexts, the challenges of providing a mucosal tissue dressing are similar, in that the dressing must stay in place long enough, perform its function, and not interfere with normal physiological function. Various embodiments of the present invention will also meet at least some of these objectives for purposes other than a post-tonsillectomy/adenoidectomy dressing.

BRIEF SUMMARY OF THE INVENTION

Certain embodiments of the present invention provide a method for reducing or eliminating pain after surgical procedures related to mucosal tissue, including tonsillectomy, adenoidectomy, or other pharyngeal operations.

Certain embodiments of the present invention provide a biodegradable film or covering that serves as a mechanical barrier to reduce pain caused, for example, by friction between solid food and healing tissue in the first few days after surgery.

Some embodiments may include one or more therapeutic substances for locally reducing pain, facilitating healing and/or otherwise treating mucosal tissue at or near a tonsil bed. In some embodiments, multiple layers of tissue dressing may contain different therapeutic substances. Some embodiments may allow a physician to inject or otherwise apply one or more therapeutic substances to a tissue dressing before applying the dressing to the patient.

In some embodiments, a tissue dressing may be applied to areas other than a tonsil bed and for purposes other than easing post-tonsillectomy pain and discomfort. For example, in some embodiments, a tissue dressing may be applied to a nasal septum to facilitate or enhance a nasal septoplasty procedure. In various embodiments, a tissue dressing may be applied at any of a number of locations in a nasal or paranasal cavity, in paranasal sinuses, in polyps located in the nasal or paranasal cavity, in a Eustachian tube, in a mouth or the like, for performing any number of functions. For example, the tissue dressing may be placed as a therapeutic drug delivery vehicle. In some embodiments, the tissue dressing may be used to stiffen or fortify soft tissues, such as for treating sleep apnea. In other embodiments, the tissue dressing may be used to cover or plug up cerebrospinal fluid (CSF) leaks. In still other embodiments, a tissue dressing may be used as an iontophoresis pad through which electrical energy may be passed. These and other embodiments are described further below with reference to the attached drawings.

BRIEF DESCRIPTION OF SEVERAL VIEWS OF THE DRAWINGS

FIG. 1 illustrates a perspective view of a dressing, according to one embodiment of the present invention.

FIG. 2 illustrates a perspective view of a two layer dressing, according to one embodiment of the present invention.

FIG. 3 illustrates a perspective view of a multilayer layer dressing, according to one embodiment of the present invention.

DETAILED DESCRIPTION OF THE INVENTION

Figure 4:
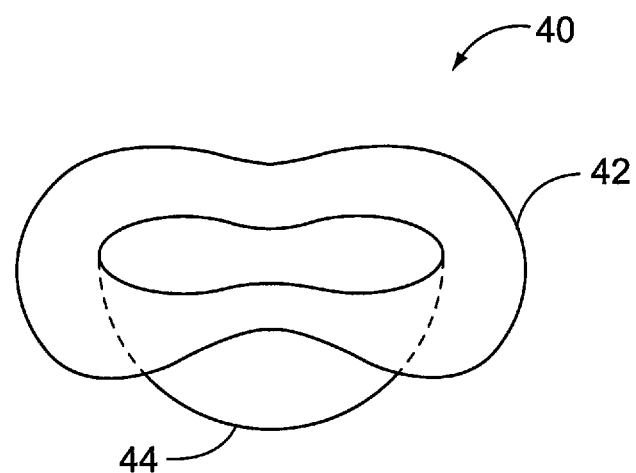
FIG. 4 illustrates a perspective view of a tissue dressing having an alternative shape, according to one embodiment of the present invention.

Various embodiments of the present invention generally comprise a mucosal tissue dressing for applying to mucosal tissue. In some cases, the tissue dressing may be applied after a surgical excision of tissue, such as in a tonsillectomy or adenoidectomy procedure, while in other cases it may be applied to tissue that has not been operated upon. In various embodiments, the dressing may have any of a number of suitable configurations, some of which are described further below. The dressing may also include one or more therapeutic substances, which it may deliver to tissue to which it is applied and/or to surrounding tissues.

Certain embodiments of the present invention are useful for reducing post-operative pain associated with surgery performed on or near mucosal tissue. It may be desirable for dressings made and used according to certain embodiments of the present invention to carry out some or all of the following functions and have some or all of the following desirable properties:

The dressing can be applied intraoperatively, quickly and easily, immediately after completion of surgery at the site.

The dressing can be readily adapted for use following a medical or surgical procedure, such as tonsillectomy or adenoidectomy.

The dressing forms a mechanical barrier that is sufficient to shield the healing tissue from abrasion, such as that due to swallowing of solid food.

The dressing has some flexibility in both dry and wet conditions. The dressing conforms easily to complex shapes.

The dressing includes a hydrated film that does not swell excessively and is both elastic and flexible after adhesion to tissue.

The dressing includes a film that sets and/or adheres rapidly to moist tissue and is firm and not tacky when set.

The dressing adheres to the surgical bed for 12 hours to 5 days.

The dressing stays intact and in place for a minimum of 48 hours.

The dressing is completely dissolved by 10-14 days.

The dressing does not swell to create an obstruction or become uncomfortable.

The dressing begins to dissolve slowly with no risk of release of large material fragments that cause a choking hazard or other complication.

The dressing does not delay healing and in some embodiments may facilitate healing.

In oral applications, the dressing does not taste bad. In some applications, the dressing may even be flavored.

The dressing provides a "cool" sensation.

The dressing is made of inexpensive materials.

Embodiments of the present invention disclosed herein may contain some or all of these properties and perform some or all of these functions.

Certain embodiments of the present invention are applied to a surgical bed like a bandage or a dressing. The dressing can be preshaped and/or cut to a custom size and shape. The bandage embodiments can have a removable backing, which reveals an adhesive layer when removed. The dressing may provide a platform useful for drug delivery or the release of other therapeutic substances.

Generally, a mucosal tissue dressing may perform adhesive, barrier, mechanical and/or dissolving functions in various embodiments. In many embodiments, a tissue dressing may perform a local function, such as reduction of pain and discomfort, reduction of bleeding, reduction of CSF leakage and/or the like. In some embodiments, a tissue dressing may alternatively or additionally also perform a central function, such as delivering a drug to the blood stream or central nervous system. In various embodiments, the tissue dressing may provide a platform for drug delivery for a variety of respiratory and/or ear, nose and throat ("ENT") diseases or conditions and may be applied to any mucosal surface. In one embodiment, for example, a tissue dressing may be used as an adhesion barrier within the nasal cavity or sinuses to prevent iatrogenic fusing of tissue after surgery. In another example, the tissue dressing may be applied to surfaces that are the site of recurrent polyps to provide a barrier to recurrence either mechanically or through sustained drug delivery.

FIG. 1 illustrates a perspective view of one embodiment of the present invention. Dressing 100 has an adhesive surface 110 and a barrier surface 120. Adhesive surface 110 is designed to contact and adhere to tissue, such as mucosal tissue or mucous membranes. Adhesive surface 110 can be textured to facilitate adhesion to tissue. Adhesive surface 110 can have textures such as fibrous, porous, dimpled, striated or other textures, including combinations thereof. Adhesive surface textures may also be selected to facilitate healing and to facilitate removal of dressing 100 in certain embodiments where removal is part of the method of treatment.

Referring still to FIG. 1, barrier surface 120 is designed to provide resistance to mechanical forces, such as abrasion. Barrier surface 120 can also provide resistance to infiltration or diffusion of substances from the biological milieu surrounding the site where the dressing is applied. Barrier surface 120 may be lubricious to prevent adhesion of foreign particles such as food. Barrier surface 120 can have textures, such as those described for adhesive surface 110 or others. Barrier surface textures may be selected to discourage adhesion of materials to dressing 100. Both the barrier surface texture and the adhesive surface texture may be selected to facilitate dissolution of dressing 100 in certain embodiments where dissolution is part of the method of treatment.

FIG. 2 illustrates a perspective view of one embodiment of the present invention. Dressing 200 has an adhesive layer 210 and a barrier layer 220. Adhesive layer 210 can be structured to promote tissue adhesion. For example, adhesive layer 210 may have a porous structure that facilitates penetration of tissue into the layer. Generally, high surface area contact between two surfaces promotes adhesion. Any structure that increases the surface area contact between the surgical bed and adhesive layer 210 may be useful.

Referring again to FIG. 2, adhesive layer 210 can be structured to tailor its dissolution rate. Some materials, such as polyanhydrides, dissolve from their surface. Other materials, such as poly($\alpha$-hydroxy esters), dissolve from their bulk. For both surface-eroding and bulk-eroding materials, control of the surface area can have an impact on the dissolution rate. A preferred structure for adhesive layer 210 can balance the surface area requirements for adhesiveness with those for dissolution. Also, as described in more detail below, surface area can have an effect on the drug delivery profile of the dressing. A preferred structure for adhesive layer 210 can take the drug delivery effects into account as well.

Still referring to FIG. 2, adhesive layer 210 includes an adhesive surface 215, which is designed to contact and adhere to tissue. Adhesive surface 215 may be textured as described above in reference to FIG. 1.

Again referring to FIG. 2, barrier layer 220 may be structured to promote mechanical durability and resistance to infiltration. Recalling that dressings of certain embodiments of the present invention may be flexible, barrier layer 220 may have a structure that provides flexibility and durability, to allow for natural tissue movement during swallowing without damage from the passage of solid food. As with adhesive layer 210, barrier layer can be structured to tailor its dissolution rate. Barrier layer 220 may be made from a surface-eroding or a bulk eroding material, or a combination thereof. Thus, a preferred structure for barrier layer 220 can balance the structural requirements for mechanical durability with those for dissolution. Since barrier layer 220 can also act as a reservoir for drug delivery, a preferred structure for barrier layer 220 can take the drug delivery effects into account as well.

Still referring to FIG. 2, barrier layer 220 includes a barrier surface 225, which is designed to provide resistance to penetration by mechanical forces, foreign particles or bacteria and infiltration of surrounding tissue components. Barrier layer 220 and/or barrier surface 225 can provide shock absorbing properties. Barrier surface 225 may be textured as described above in reference to FIG. 1.

The total thickness of the dressing can be in a range from about 0.1 mm to about 0.7 mm. The preferred thickness of certain embodiments is about 0.3 mm. The adhesive layer thickness can be about 0.1 mm and the barrier film thickness can be about 0.2 mm. In certain embodiments, the thickness of the dressing may not be uniform. For example, in certain embodiments, the edges of the dressing may be thinner than the center of the dressing.

FIG. 3 illustrates a perspective view of one embodiment of the present invention. Dressing 300 is composed of adhesive layer 310 and barrier layer 330. Connecting layer 320 connects adhesive layer 310 and barrier layer 330. Connecting layer 320 can be structured as previously described with regard to adhesive layers and barrier layers. That is, connecting layer 320 can have a structure that is tailored to produce a certain dissolution rate. Further, connecting layer 320 can act as a reservoir for drug delivery. A preferred structure for connecting layer 320 is tailored to provide the desired dissolution rate and drug delivery rate.

Referring still to FIG. 3, adhesive layer 310 and barrier layer 330 may each be structured as described in reference to FIG. 2. In certain embodiments, when adhesive layer 310 is structured to provide adhesiveness and barrier layer 330 is structured to provide mechanical durability, connecting layer 320 can be structured to provide a durable bond between the two layers. That is, the structure of adhesive layer 310 may be highly porous, for example, while the structure of barrier layer 330 may be densely packed, for example. Connecting layer 320 may provide a structural gradient between these two different structures to form a durable connection between the layers.

FIG. 3 illustrates a three layer dressing. The dressings of certain embodiments of the present invention may be composed of more than three layers. The adhesive layer of certain embodiments may be comprised of several layers, each having a structure and composition the same as or different from another layer. Each layer in a set of adhesive layers may be structured to achieve specific properties. Similarly, the connecting layer and the barrier layer may each be comprised of several layers, each having a structure and composition the same as or different from another layer. In certain embodiments, one or more layers of the dressing may be colored to provide ease of use and/or to identify the different layers. In some embodiments, part or all of the dressing may be colored to help a physician and/or patient to confirm that the dressing is still in place, how much of the dressing has dissolved or the like.

In a number of embodiments, one or more layers of a mucosal tissue dressing may be configured to hold and elute one or more therapeutic or other substances. For example, steroids, anesthetics, anti-inflammatory medications, mucolytics, antibiotics and many other substances may be introduced into a layer of a mucosal tissue dressing so as to elute out of the dressing at a desired rate once it is applied to tissue. Many diseases are localized to a specific part of the body and are most effectively treated with therapy targeted directly to the disease site. The local delivery provided by a drug eluting mucosal tissue dressing may allow for higher therapeutic concentrations of drug where it is needed and may prevent many unwanted systemic side effects.

Diseases along the digestive tract are often difficult to target due to a mucosal surface that does not encourage binding of standard dressing materials and a constant flux of digestive juices that work to both degrade and wash away mucoadhesive drug delivery products. Various embodiments of the present invention may involve a mucoadhesive film that may include a drug delivery aspect and a barrier layer that allows for prolonged drug delivery. Diseases of the digestive tract that may benefit from this therapeutic drug delivery method include:

Diseases or treatments of the oral cavity such as oral *candida* infection (thrush), xerostromia (dry mouth), post surgical management of pain and infection, oral cancer, halitosis, delivery of fluoride, softening of gums during orthodontic treatment and the like.

Diseases or treatments of the throat such as tonsillitis or post-surgical management of tonsillectomy or other throat surgical procedures, treatment of vocal cord dysfunction such as paralysis or polyps, laryngeal cancer and the like.

Diseases or treatments of the gastro-intestinal tract such as gastric ulcers, gastritis, reflux disease, cancer, *helicobacter pylori* infections, proton pump dysfunction, obesity and the like.

In various embodiments, drug may be incorporated into the dressing at the time of manufacture or at the time of application. The dressing may be biodegradable or it may be non-degradable and removed as needed. One or more drugs may be incorporated into the same film and delivered on the same or different release schedules. The dressing may be applied manually or with the use of endoscopy tools. The dressing may be designed to release drug either toward the mucosal surface or into the oral/laryngeal/gastro-intestinal tract.

Drug delivery to mucosal surfaces has been hampered by the lack of film forming agents that can effectively bind that tissue and remain in place for a sufficient time to deliver therapy for the period needed. A large number of oral dressing materials have been developed such as SaliCept Oral Patch by Carrington Laboratories and Gelclair Oral gel by Sinclair Pharmaceuticals. These materials adhere to oral mucosa but they dissolve in a matter of minutes and so are not useful for prolonged delivery of therapeutic agents.

In various embodiments, a mucosal dressing of the present invention may adhere firmly to mucosal surfaces and remain in place for a period of days to weeks. In some embodiments, the dressing may be directly placed over the site of a gastro-intestinal ulcer or lesion and may provide prolonged continuous drug delivery to that site. In some embodiments, the mucosal dressing may be placed endoscopically into the gastro-intestinal tract.

If the dressing material is designed not to degrade, then the drug delivery system can also be removed and drug delivery terminated if necessary. The dressing may include a barrier layer that prevents dissolution of the material by the acidic contents of the digestive tract. Similarly, the barrier layer may prevent the dressing from interacting with food, essential nutrients or orally administered drugs in the digestive tract.

In some embodiments, a therapeutic substance may be designed to pass through the blood brain barrier (BBB) to enter the central nervous system (CNS). The most important factor limiting the development of new drugs to treat CNS disease is the BBB that limits penetration of most CNS drug candidates. One location where the BBB does not function to limit penetration is at the interface between the nasal epithelium and the brain. When delivered from the nasal epithelium, CNS drug concentration may exceed systemic plasma concentrations. Delivery from the nose to the CNS also occurs along both the olfactory and trigeminal neural pathways and additionally targets nasal associated lymphatic tissues and deep cervical lymph nodes. Thus, delivery of drugs through the nasal mucosa may be one way to target the CNS and or lymph nodes.

Some of the CNS diseases that may be addressed using intranasally administered drugs eluted from a mucosal tissue dressing of the present invention include Alzheimer's disease, Parkinson's disease, brain cancer, stroke, migraine, psychoses, epilepsy, meningitis, memory loss or other forms of neurodegeneration, lymphoma, neuroAIDS, various addictions, certain forms of obesity and the like. Drug formulations may include, for example, nasal sprays and muco-adhesive microemulsions, some of which may be developed in the future.

A tissue dressing of the present invention, in some embodiments, may be used to provide localized and controlled drug delivery selectively to the CNS. The drug may be encapsulated into the dressing at the time of manufacture or it may be added to the dressing at the time of placement on the nasal or sinus mucosa. Additional drug may be added as needed at a later time in some embodiments of this invention. The dressing may be bioresorbable and eventually degrade so that it does not have to be removed, or it may be non-absorbable and removed as needed for replacement or cessation of therapy.

A drug delivered from a mucosal dressing will be delivered much more locally at the site of placement and can be directed downward into the mucosal tissue rather than into the airway. Not all drugs can be easily formulated so as to be aerosolized and the formulation usually requires additional excipients with the potential for adverse effects, particularly on mucosal tissue. Nasal sprays will likely require repeat administration of relatively high doses so as to achieve a therapeutic dose at the target site and to maintain that dose within the therapeutic range between administrations. In contrast, a mucosal dressing may deliver drug at a steady or controlled rate continuously for as long as it is needed. This generally allows for delivery of lower doses and does not cause "peak and valley" drug concentration changes over time. In some embodiments, the drug reservoir may be replenished with drug at a later time if necessary for continued therapy or it may be removed if there is a need to quickly halt therapy. Novel drug delivery films are now under development that allow for delivery of more than one drug simultaneously but at different rates based on their pharmacokinetic profile.

In some embodiments, a drug delivery dressing may be applied as a preliminary evaluation of drug effectiveness to treat a CNS condition prior to a more invasive drug delivery technique. In this way different therapeutic candidates can be screened for potential effectiveness in an individual patient before they are subjected to a risky surgical procedure.

The preceding discussion highlights certain features, characteristics, and/or properties of mucosal tissue dressings. Many of these features will be useful in certain of the specific embodiments described below.

FIG. 4 illustrates an alternative embodiment of a tissue dressing 40 having a curved shape to conform to a tonsil bed from which a tonsil has been removed. Dressing 40 has an outer rim 42 configured for placement on normal, non-operated tissue surrounding the tonsil bed and a concave central region 44 configured to conform to the tonsil bed. Outer rim 42 may be the same thickness as central region 44, or outer rim 42 may be thinner than central region 44. In some embodiments, outer rim 42 is thicker than central region 44. Outer rim 42 can help dressing 40 stay in place by providing increased contact area with healthy tissue.

Still referring to FIG. 4, dressing 40 may have different shapes and sizes that are adapted for use in surgical beds and/or patients of various sizes. Dressing 40 may come in a range of predetermined shapes and sizes. For example, dressing 40 may have a range of sizes of central region 44 in which the depth, diameter, and/or radius of curvature may vary. Similarly, outer rim 42 may have a range of diameters. A physician can select an appropriately sized and shaped dressing for placement following surgery. Alternately, a physician can shape dressing 40 to create a custom fit to a patient's surgical bed. In another alternate embodiment, a physician can combine an outer rim 42 of specific shape and size with a central region 44 of specific shape and size to form a customized dressing.

Referring again to FIG. 4, outer rim 42 and central region 44 may be formed of the same material or of different materials. The materials and/or texture of outer rim 42 can be chosen to minimize irritation or injury to the healthy tissue on which it is placed. The materials and/or texture of central region 44 may be chosen to facilitate healing of the surgical bed. Central region 44 and/or outer rim 42 can also include therapeutic or other agents.

Figure 5:
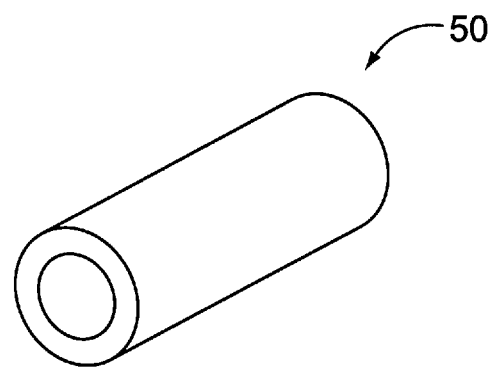
FIG. 5 illustrates a perspective view of a cylinder-shaped tissue dressing, such as for use in or near a Eustachian tube, according to one embodiment of the present invention.

FIG. 5 illustrates an alternative embodiment of a tissue dressing 50 in which the dressing has a cylindrical shape.

Cylindrical dressing 50 can be used in or near tubular body cavities, such as, for example, a Eustachian tube. Fluid in the Eustachian tubes is a common problem, and a dressing having certain characteristics may be useful in Eustachian tube treatment. For example, cylindrical dressing 50 may be placed at the base of the Eustachian tube and may deliver one or more therapeutic substances, such as a steroid or a surfactant. Cylindrical dressing 50 can be designed to act as a one-way valve to allow flow out of the Eustachian tube but not into it. Cylindrical dressing 50 can be designed to absorb fluid, or may perform some combination of these or other functions. The choice of materials, structure, and texture for the walls of cylindrical dressing 50 will affect the function and properties of the dressing, as is disclosed elsewhere in this document.

Figure 6:
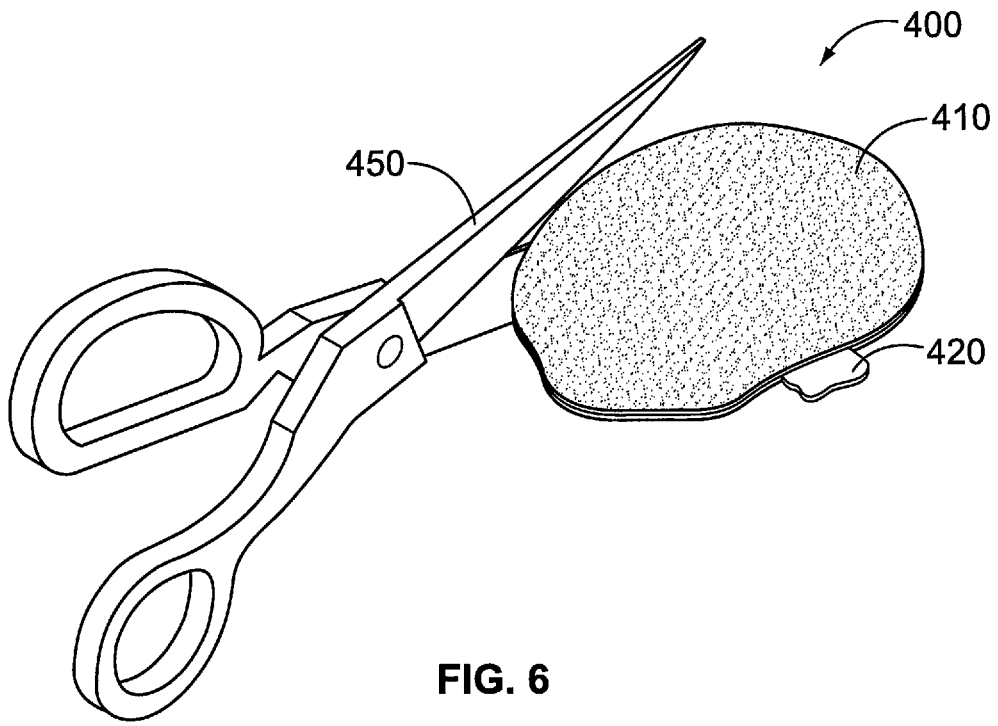
FIG. 6 illustrates a method of preparing a dressing for use, according to one embodiment of the present invention.

FIG. 6 illustrates one embodiment of the present invention in which a dressing is customized for application to a surgical bed. Dressing 400 has a barrier surface 410 and an optional backing 420. In certain embodiments of the present invention, the dressing may have a backing on its adhesive surface, its barrier surface, or both. In the embodiment illustrated in FIG. 6, backing 420 covers the adhesive surface (not numbered) of dressing 400. Backing 420 is illustrated as having an optional tab to facilitate removal. A backing can preserve the integrity of the adhesive surface or the barrier surface prior to use. A backing can also prevent premature release of any agents from the dressing.

Referring still to FIG. 6, scissors 450 can be used to cut dressing 400 into a custom shape to match the surgical bed. Dressing 400 may come in preshaped configurations, such as a butterfly shape, a lobed shape, a triangular shape, or any other conventional bandage shape. Dressing 400 may also have a curved shape or another shape extending out of the plane of the dressing. Additionally, dressing 400 may be moldable such that when manipulated by a user, dressing 400 retains the shape its molded shape. The materials selected for the adhesive, barrier, and connecting layer (if present) may provide this moldable property.

In certain embodiments of the present invention, an adherent material is applied onto post-surgical beds to cover and protection them from abrasion by food or other items. The sticky material can be a polymer. Application of the material can be by spraying, wiping, painting or other method. The surgical bed is protected from mechanical disruption or irritation. Additionally, the barrier may protect the surgical bed from infiltration by pathogens or other harmful infiltrates. The dressing may provide a platform useful for drug delivery or the release of other therapeutic substances.

Figure 7:
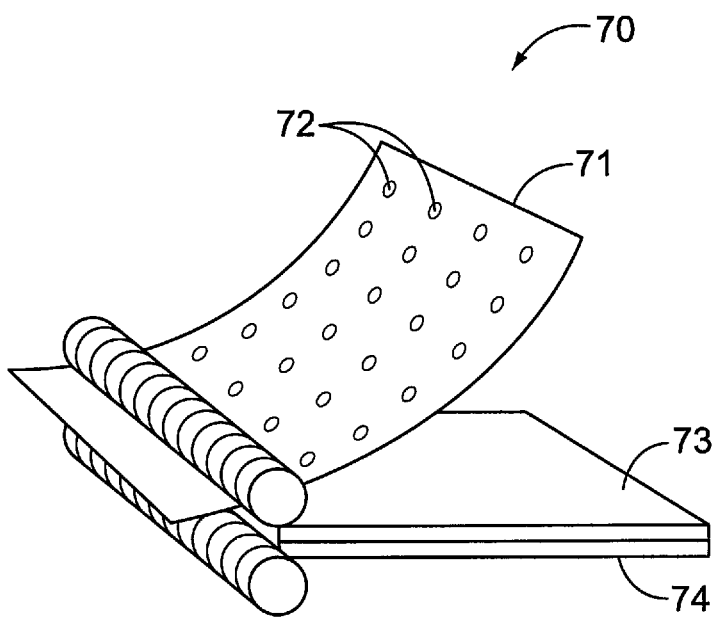
FIG. 7 illustrates a method of packaging and preparing a multi-layer dressing for use, according to one embodiment of the present invention.

FIG. 7 illustrates a tissue dressing 70 and a method for packaging the same. In this embodiment, tissue dressing 70 includes a tissue adherent layer 71 which includes one or more apertures 72. Tissue dressing 70 may also include an absorbent layer 73 and a barrier layer 74. Adherent layer 71 has an outer surface capable of adhering to mucosal tissue and an inner surface capable of adhering to absorbent layer 73. Adherent layer 71 is made from materials suitable for these purposes as described elsewhere in this application. Absorbent layer 73 is designed to absorb therapeutic or other agents prior to placement in a surgical bed and to allow those agents to elute out over time. Absorbent layer 73 can have a porous structure (including macroporous, microporous, or nanoporous structures) to facilitate the uptake and release of agents. Certain materials may be preferred over other materials for use with specific agents. For example, a hydrogel material may provide a suitable elution profile for a hydrophilic agent, while a more hydrophobic material may provide a suitable profile for a hydrophobic agent. Barrier layer 74 can provide a structural backing for absorbent layer 73, promote resistance to mechanical abrasion on the outer surface of tissue dressing 70 once it is applied to the surgical bed, and provide a barrier to elution of the agent such that the agent preferentially elutes through adhesive layer 71 (and/or through apertures 72).

Referring still to FIG. 7, although the entire tissue dressing may be packaged together, in certain embodiments adherent layer 71 can be packaged separately from absorbent layer 73 and/or barrier layer 74. In certain embodiments, and in particular those embodiments in which adherent layer 71 is packaged separately, a physician may add a therapeutic or other agent to absorbent layer 73 and then apply adherent layer 71 to absorbent layer 73. Thus, packaging adherent layer 71 separately allows for customized agent selection, including customized dosing. The therapeutic or other substance may be added in any suitable way, such as by injecting with a syringe, pouring out of a container, spraying or the like. In alternative embodiments, all three layers 71, 73, 74 may be separate and may be coupled together by the physician or other user. In some embodiments, different absorptive layers 73 may be prepackaged containing different therapeutic or other substances, so the physician may select an absorptive layer 73 depending on his/her needs for a particular patient. In alternative embodiments, barrier layer 74 may be packaged separately from adherent layer 71 and absorptive layer 73.

In some embodiments, whichever layer is applied to the others may act to seal in whatever therapeutic or other substance is introduced into absorptive layer 73. This sealing may allow tissue dressing 70 to act like a fillable reservoir that elutes a substance over time. As discussed above, the layer that is applied to the other layers and that seals in substance may be tissue adherent layer 71, barrier layer 74, or even some other layer in alternative embodiments. In some embodiments, the sealing layer may be impermeable, so that loaded therapeutic or other substance(s) must elute through a different layer or through one or more openings in a layer. Alternatively, the sealing layer may be permeable or semi-permeable, so that while it seals in the loaded substance initially, it allows elution of the substance over time.

Figure 8A:
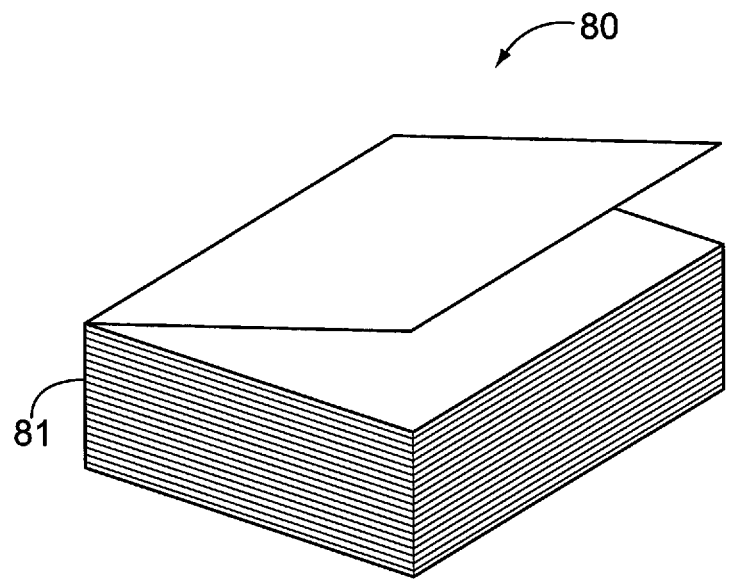
FIGS. 8A and 8B illustrate methods of packaging a dressing for use, according to alternative embodiments of the present invention.
Figure 8B:
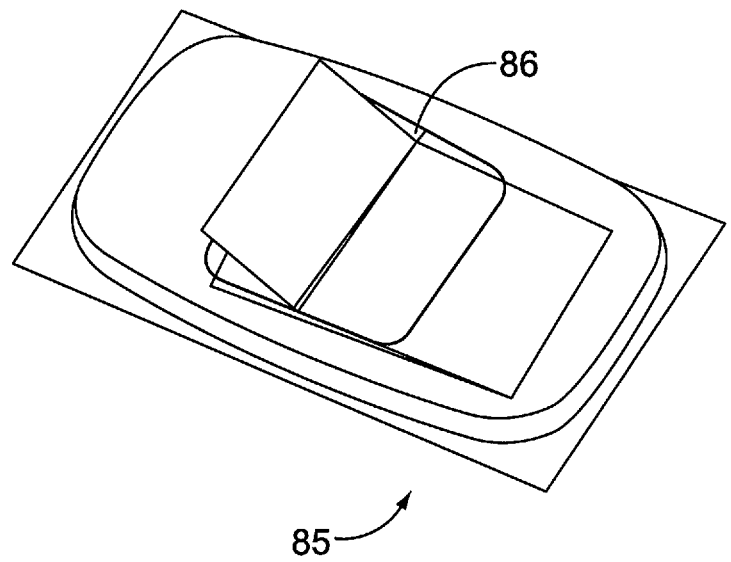

FIGS. 8A and 8B illustrate alternative methods of packaging dressings for use, according to certain embodiments. Referring to FIG. 8A, multiple tissue dressing may be packaged into a stack 80 joined at a stack edge 81. A user can remove one tissue dressing at a time from stack 80 for use. Similarly, referring to FIG. 8B, multiple tissue dressings may be stored in dispenser 85 and removed through dispenser slot 86.

Figure 9:
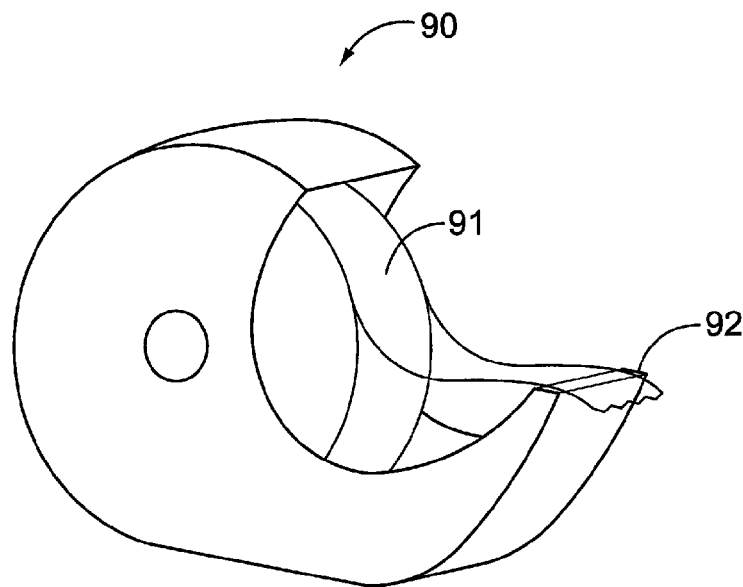
FIG. 9 illustrates a method of packaging a dressing for use, according to an alternative embodiment of the present invention.

FIG. 9 illustrates another method of packaging tissue dressings for use, according to certain embodiments. Dispenser 90 includes a roll 91 of tissue dressings which can be removed and cut to an appropriate size using cutting edge 92. A physician can select an appropriate size for a tissue dressing from roll 91.

Figure 10:
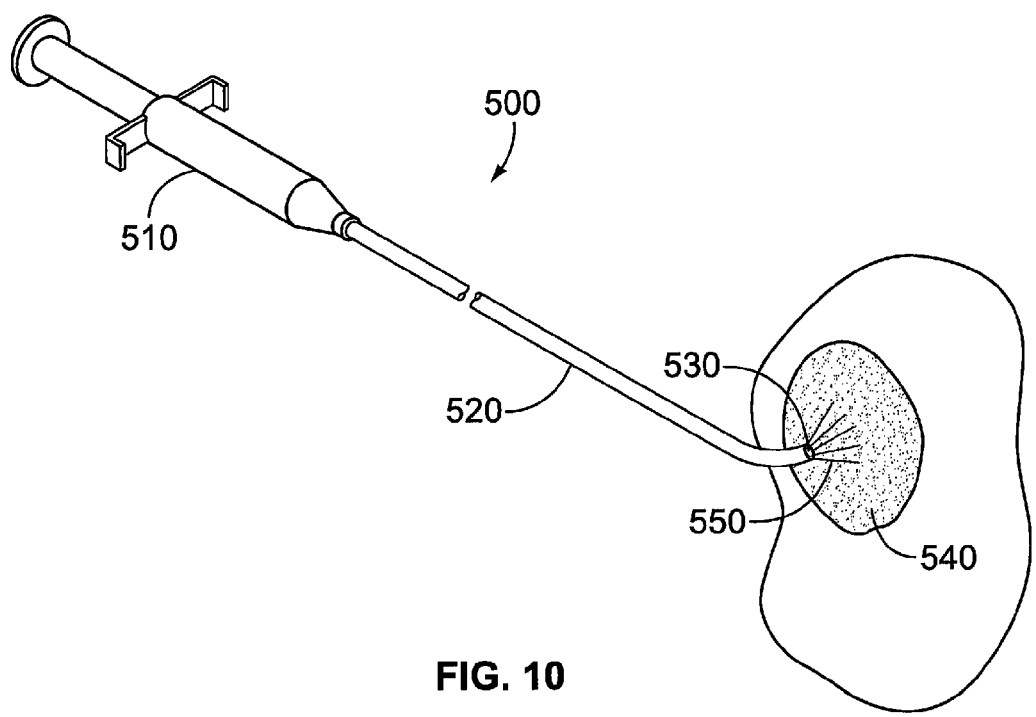
FIG. 10 illustrates a device and method useful in applying an in-situ dressing, according to one embodiment of the present invention.

FIG. 10 illustrates one embodiment of the present invention in which the dressing is applied and formed in situ on the surgical bed. Device 500 includes reservoir 510, elongate member 520, and distal end 530. Reservoir 510 holds at least one material in a deliverable form, such a liquid or gel. Reservoir 510 may be a syringe barrel or similar device. Reservoir 510 connects to elongate member 520. Elongate member 520 has at least one lumen through which the material contained in reservoir 510 can pass. Elongate member 520 can be flexible, rigid, or a combination. The desired flexibility or rigidity of elongate member 520 depends in part on the treatment site. For example, a treatment site in a remote body lumen may require a flexible elongate member capable of providing access through tortuous anatomy.

Still referring to FIG. 10, the material from reservoir 510, flowing through elongate member 520, is applied to the treatment site through distal end 530. Distal end 530 can have a cross sectional dimension approximately the same as a cross sectional dimension of the lumen of elongate member 520. Alternatively, distal end 530 may taper or flare so that it has different dimensions than the lumen of elongate member 520. Also, distal end 530 can be configured to provide a specific spray pattern. For example, distal end 530 can be configured as an end cap with a pattern of holes. In FIG. 10, spray pattern 550 is used to form layer 540.

Also, distal end 530 can be malleable, such that a user can pre-shape an angle that distal end 530 forms with elongate member 520 to direct the application of material. Distal end 530 can be steerable, providing the user with the ability to control the direction of spray application after the device has reached the treatment area.

While distal end 530 is capable of applying material in spray pattern 550, it can also apply material in any way that a liquid, gel, or other material can be applied. For example, a liquid or a gel may seep, weep, or ooze from distal end 530. Known devices suitable for applying material include needles, cannulas, and catheters. Other devices capable of painting or wiping material onto a surgical bed, such as a swab, are also useful.

In one embodiment, a sprayable or flowable tissue dressing material may be applied areas other than post-tonsillectomy/adenoidectomy surgical beds. Dressing materials applied in such other areas can have different properties or characteristics than post-tonsillectomy/adenoidectomy dressings in order to perform the function required in such other areas. For example, a flowable tissue dressing may be applied before a surgery on mucosal tissue to reduce bleeding and oozing after the procedure. In another embodiment, a sprayable material may be applied inside a paranasal sinus to reduce or stop ciliary movement and thus to keep a drug that has been delivered to the sinus from being moved/flushed out of the sinus by ciliary action. A sprayable or flowable dressing may also be used to plug CSF leaks, just as a solid film may also be used.

Figure 11A:
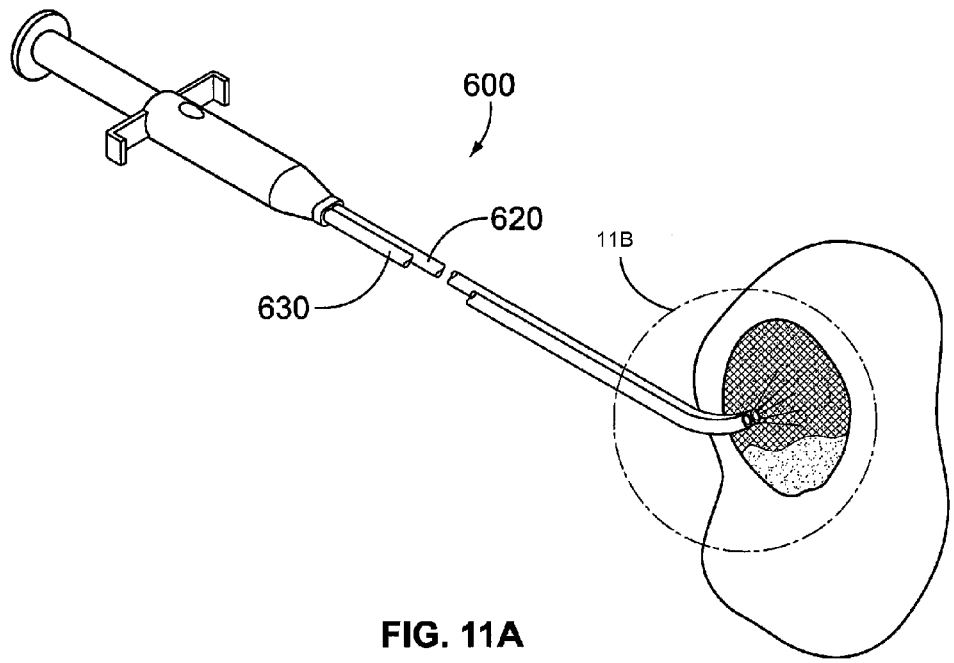
FIG. 11A illustrates a device and method useful in applying an in-situ dressing and FIG. 11B illustrates a close-up view of a section of the same device and method, according to one embodiment of the present invention.
Figure 11B:
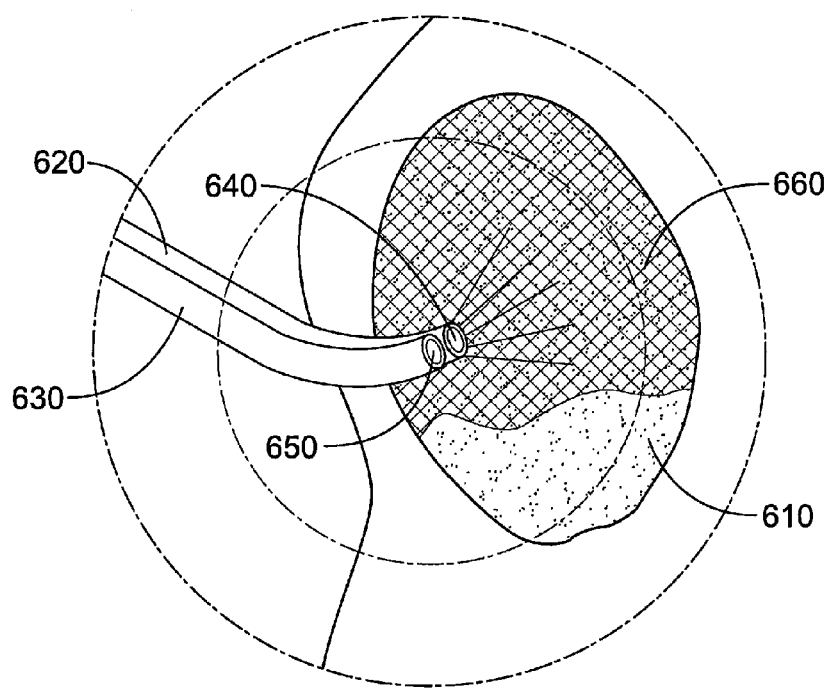

FIGS. 11A and 11B illustrate another embodiment of the present invention in which the dressing is applied and formed in situ on the surgical bed using an energy source. Distal part 600 of the device includes elongate tubular member 620 and elongate conductor 630. Elongate tubular member 620 is similar to elongate member 520 in that it can connect to a reservoir and can be used to supply and apply material to a treatment site. Elongate conductor 630 is shown coupled to elongate tubular member 620, although in certain embodiments elongate conductor can be a separate device. Elongate conductor 630 is capable of conducting energy, such as ultraviolet light, visible light, infrared light, radiofrequency energy, sound waves (including ultrasound), heat, other forms of energy, or combinations thereof. Elongate conductor 630 may also be used to provide a vacuum or promote air flow over the dressing to facilitate drying, curing, or adhesion of the material. Elongate conductor 630 has distal conductive end 650, which can focus or target the energy conducted along elongate conductor 630. Distal conductive end 650 can be a lens, for example. The energy conducted by elongate conductor 630 is useful for curing the material applied to the treatment site into a layer, such as dressing layer 660.

Referring to FIG. 11B, dressing layer 660 is formed of the liquid, gel or other material applied to the treatment site. In certain embodiments, the applied material can be transformed from one state to another, for example, from liquid to gel, from liquid to solid, from gel to solid, or any combination thereof. Such transformations can be termed "curing" and include those conventionally known as gellation, solidification, polymerization, and processes equivalent to each such transformation. These transformations can be carried out in any of the conventionally known ways. For example, a polymerization of a liquid into a gel or solid at the treatments site may occur when the applied material contacts fluid at the treatment site, as can happen with N-vinyl-2-pyrrolidine (NVP). Or, polymerization at the treatment site can be carried out by applying both a polymerizable liquid and a polymerizing agent, such as linear polyethylene oxide. Similarly, gellation at the treatment site can be carried out by applying both a gellable liquid (or gel) and a gelling agent, such as NVP.

In certain embodiments of the present invention, the dressing can contain drugs or active substances that can be released into the local tissue environment. Examples of suitable drugs or active substances include anti-inflammatories, antibiotics, analgesics, anesthetics, and combinations thereof. Specific examples of suitable drugs or active substances include *eucalyptus*, lidocaine, or steroids. Certain embodiments of the present invention can include substances that promote tissue adhesion, such as growth factors or RGD peptides. Such adhesion promoting substances can be preferentially located in an adhesive layer or on an adhesive surface of the dressing. In other embodiments, a tissue dressing may include drug to help prevent post-surgical tissue adhesion. Certain embodiments can include substances that discourage bacterial adhesion or colonization or the accumulation of debris, such as colloidal silver or microbial toxins. Such adhesion preventing substances can be preferentially located in a barrier layer or on a barrier surface. Other embodiments of the present invention can include hemostatic agents such as fibrinogen or thrombin that can aid in the reduction of post-surgical bleeding. In some embodiments, the tissue dressing may include a drug that inhibits cell growth. For example, in some tonsillectomy cases, if a tonsil is not completely removed, the tonsil may grow back over time. If cell growth inhibition drugs are locally applied, however, such regrowth may be inhibited. If the surgical procedure involves removal of cancerous tissue, anti-cancer therapies may be included in the dressing.

Any of the substances discussed above, or any combination thereof, can be included in the preformed dressing embodiments or in the in situ formed dressing. In some embodiments, two or more therapeutic substances may be contained in and delivered from one tissue dressing. For example, a dressing with multiple layers may contain a different substance in each layer. Drug delivery mucosal tissue dressings may be placed in any suitable location in the throat, mouth, nasal cavity, paranasal sinuses or the like to perform a desired function. For example, in one embodiment, small pieces of tissue dressing containing steroid may be placed on or in nasal polyps to shrink the polyps. In another embodiment, a tissue dressing may be placed in the nasal cavity to deliver drug to the olfactory nerve and from there to the central nervous system, for example for treating Alzheimer's Disease, meningitis or the like.

Embodiments of the present invention described above may be constructed in a variety of ways. Certain manufacturing methods and materials may be suitable for various embodiments, whether they are preformed dressings or in situ formed dressings. A description of a certain method or material in reference to a specific dressing embodiment is not meant to limit that use of that method or material to that specific embodiment.

The material used in certain embodiments can be polymers. Suitable polymers may include the naturally-occurring and synthetic versions of the following: polysaccharides (including, for example, cellulose-based polymers, alginate-based polymers, chitin and chitosan based polymers, and glycosoaminoglycan-based polymers), protein polymers (including, for example, collagen, elastin, laminin, poly(amino acids) and pseudopoly(amino acids)), poly($\alpha$-hydroxy esters), polycaprolactones, poly(ortho esters), polyanhydrides, polyhyrdroxybutyrates, polyphosphazenes, polydioxanones, polyoxalates, polyethers (including, for example, polyethylene glycol, polypropylene glycol, polyethylene oxide, polypropylene oxide), polyimines, polyurethanes, poly(vinyl alcohols) and copolymers, blends and composites thereof. More generally, any biomaterial displaying one or more of the properties described herein as desirable for certain embodiments of the present invention may be suitable.

Materials may be chosen for use in certain embodiments for their ability to form a hydrogel. A hydrogel is typically formed from a polymer network in which a high volume water in dispersed. The polymer backbone is typically insoluble in water and may have polar groups appended to it to promote interaction with water. Hydrogels generally are flexible and mechanically similar to living tissue, in part due to the high water content.

Materials may also be chosen for their ability to degrade or dissolve after implantation. Many of the polymeric materials listed above are known to degrade or dissolve in vivo. As described above, the materials may surface-erode, bulk-erode, or both. Both chemical composition and the physical structure of an implanted material can affect the degradation rate. In various embodiments, surfaces and layers of the dressing will be designed such that degradation or dissolution occurs from about 48 hours to about 14 days after implantation. In certain embodiments, the adhesive layer degrades faster than the barrier layer when in contact with saliva.

Materials which may be used to form the adhesive layer and/or adhesive surface may include but are not limited to cellulose-based polymers based on ethyl cellulose, methyl cellulose, carboxymethyl cellulose, hydroxypropyl methyl cellulose or combinations thereof. Other materials for use in the adhesive layer or adhesive surface may include but are not limited to polyvinlylpyrrolidone, polypropylene glycol, hyaluronic acid, collagen, chitin, chitosan, glycosaminoglycans, proteoglycans, fibrin, fibrinogen or the like.

Materials which may be used to form the barrier layer or barrier surface may include but are not limited to polymers based on ethyl cellulose, methyl cellulose, polyethylene glycol, and polypropylene glycol.

As described above, both the adhesive surface and the barrier surface can be treated to provide adhesive or bio-resistive properties. For example, biomaterial surfaces can be chemically treated such that small molecules, peptides, proteins, or functional groups are bonded to the surface. Such surfaces can exhibit dramatically improved adhesive or bio-resistive properties. Alternatively, for example, surfaces may be treated by bombarding them with plasma or ions or other energy-driven surface modification techniques or their equivalents. Such surfaces can also exhibit dramatically improved adhesive or bio-resistive properties. Moreover, the texture of a surface can also influence its adhesive or resistive properties. Dimples or pores can be molded into a surface, machined into a surface, chemically etched, or ablated with a laser, for example. Other textures or patterns are also possible Additionally, the three-dimensional structure of an adhesive layer or the barrier layer can promote or discourage adhesion, and can promote mechanical strength. Porous layer can be formed using gas-evolution foaming techniques, incorporating and subsequently dissolving porosigens, or by phase-separation techniques. Alternatively, for example, fibrous surfaces can be produced using techniques common to the textile industry, such as weaving or felting. The size and shape of the pores and the interstices between fibers can influence the adhesiveness and mechanical properties of a layer.

Both the surface texture and the three-dimensional layer structure of certain embodiments can influence the drug delivery profile of dressings. For example, drugs or active substances that diffuse from the bulk of the layer through the surface can be delivered at a higher rate in a high surface area dressing than in a comparably sized low surface area dressing. Similarly, a higher internal porosity for a dressing results in a higher diffusion rate. Of course, many other parameters influence the drug delivery profile of an implant, such as the solubility of the drug in the polymer carrier and the solubility of the drug in the biological milieu.

Figure 12:
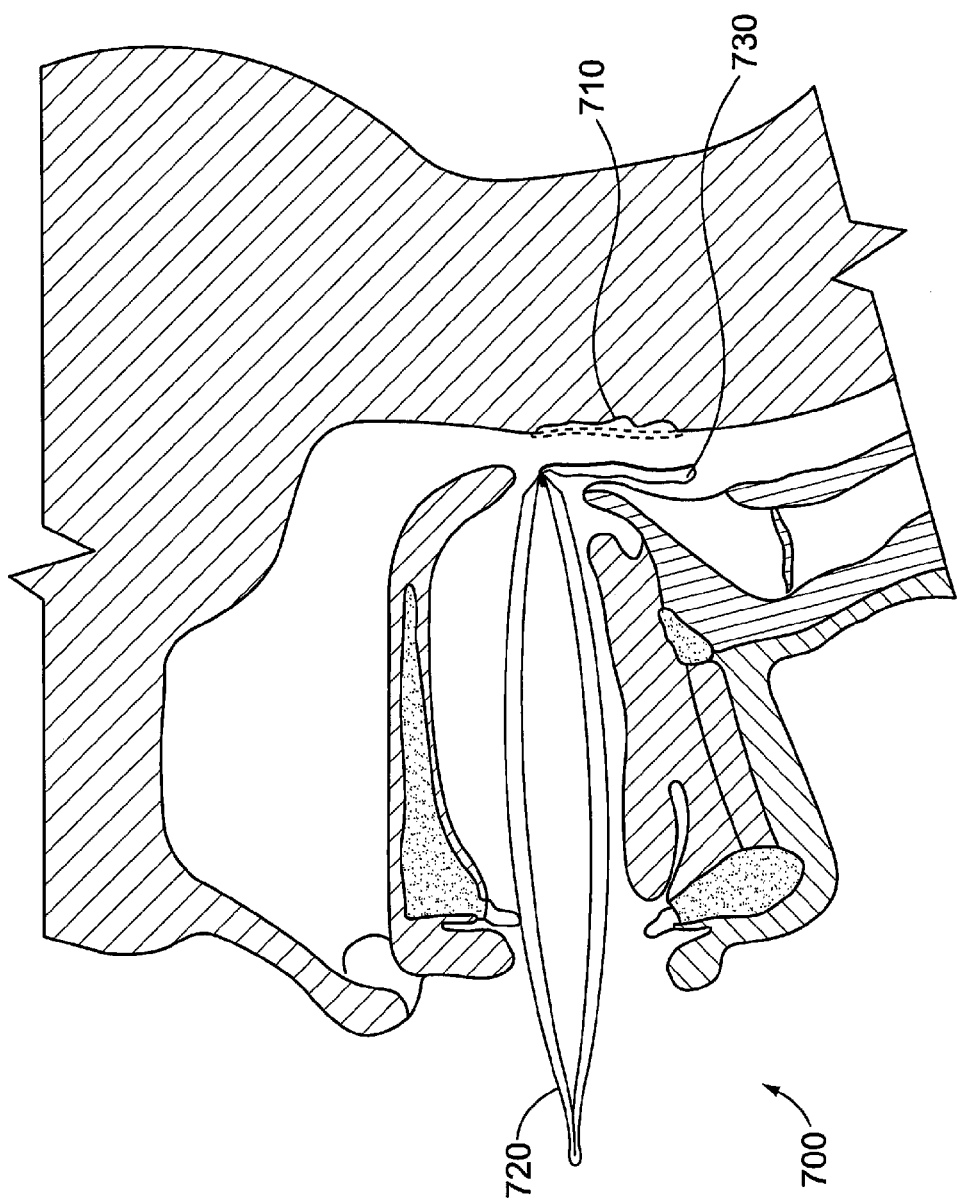
FIG. 12 illustrates a method for applying a tonsillectomy dressing according to one embodiment of the present invention.

FIG. 12 illustrates one method of use of an embodiment of the present invention in which a preshaped dressing is placed on a surgical bed. Patient 700 has a post-operative site 710, in which mucosal tissue has been damaged. After the surgical procedure has concluded, a user can apply preshaped dressing 730 to post-operative site 710 using forceps 720. As previously discussed, preshaped dressing 730 may have been cut or shaped by the user to customize it for this particular surgical bed, or it may have been provided in a shape and size already suitable for this particular surgical bed. In certain embodiments, the dressing may be applied in a dry state and made moist by the application of saline to the dressing and/or the surgical bed.

Figure 13:
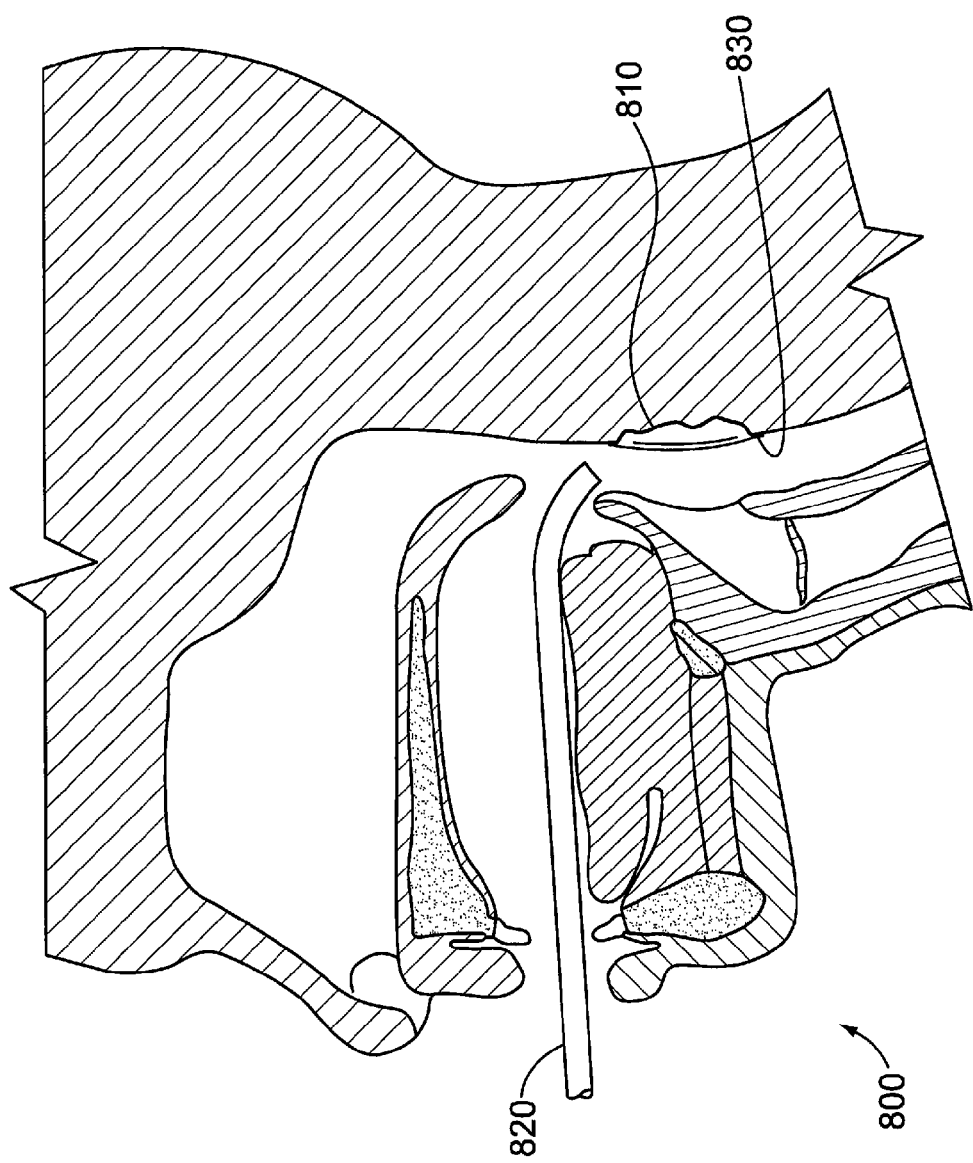
FIG. 13 illustrates a method for applying an in-situ tonsillectomy dressing according to one embodiment of the present invention.

FIG. 13 illustrates one method of use of an embodiment of the present invention in which a dressing is formed in situ on a surgical bed. Patient 800 has a post-operative site 810, in which mucosal tissue has been damaged. After the surgical procedure has concluded, a user can insert the distal section of delivery device 820 such that the distal end of delivery device 820 is near post-operative site 820. Material can be applied through delivery device 820. The material may form layers as described above. Ultimately, the applied material forms in situ dressing 830.

The devices and methods described in the various embodiments above have in some cases made particular reference to mucosal tissue associated with surgical procedures on tonsils or adenoids. However, dressings capable of treating mucosal tissue associated with surgical procedures on the sinus, turbinate, gum, cheek, pharynx, esophagus, stomach, gut, or anus are also contemplated by these descriptions.

Figure 14:
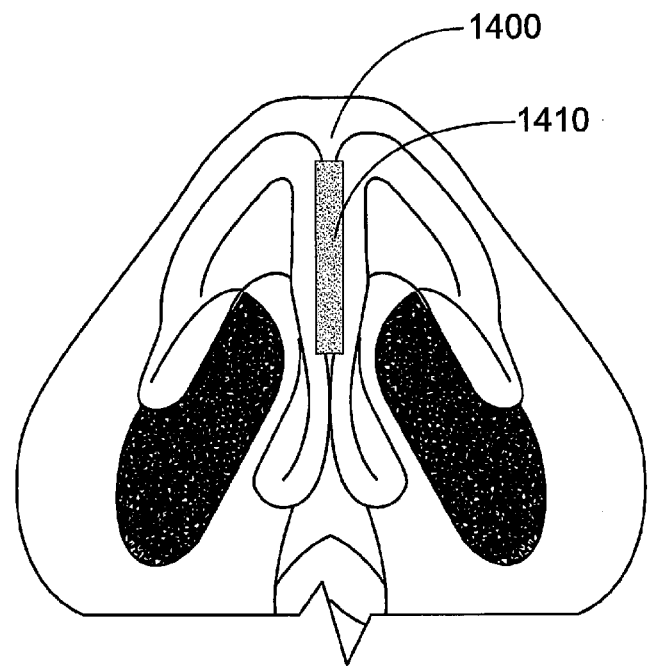
FIG. 14 illustrates a method for applying a film to a nasal septum, according to one embodiment of the present invention.

In some embodiments, a tissue dressing may be used as a support structure or to add mass to a piece of tissue for a particular function. For example, FIG. 14 illustrates the results of a method for repairing a nasal septum 1400 using a tissue support 1410. In surgical procedures to treat a deviated septum, a physician typically uses a splint or similar device to support the repaired septum. In the embodiment illustrated in FIG. 14, tissue support 1410 has been placed within, or at least partially within, repaired septum 1400. In contrast to a splint, which can be difficult to insert and maneuver and requires eventual removal from the healed septum, tissue support 1410 can add structure to the repaired septum by, in part, adhering to the tissue. Tissue support 1410 can include therapeutic, analgesic, anesthetic or other agents. Tissue support 1410 can be designed to degrade over time thereby eliminating the need for later removal.

Figure 15:
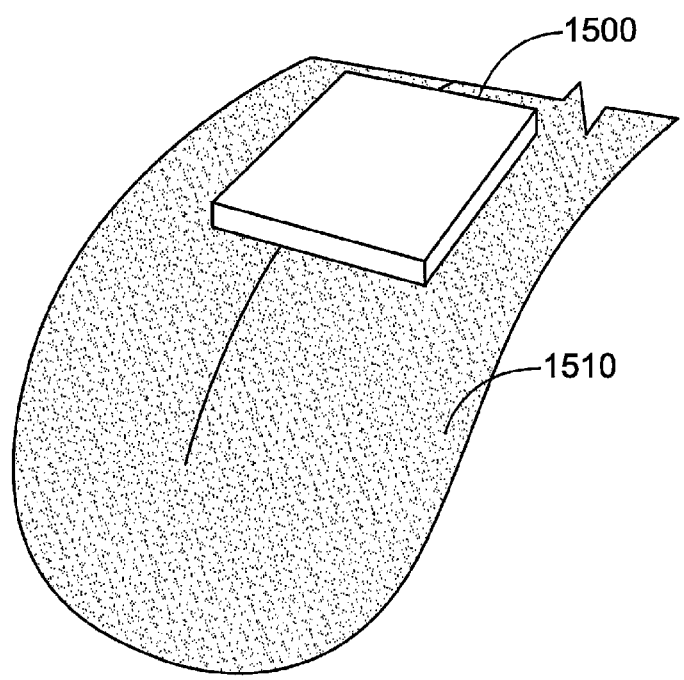
FIG. 15 illustrates a method for applying a tissue dressing to a posterior aspect of a tongue in performing a sleep apnea treatment procedure, according to one embodiment of the present invention.

FIG. 15 illustrates another exemplary embodiment in which a tissue support film 1500 is adhered to the back of tongue 1510 to make that portion of tongue 1510 more rigid. There is some evidence that sleep apnea may be caused by the tongue retracting backwards while sleeping and that a stiffer tissue in the posterior aspect of the tongue may prevent this retraction. In some embodiments, support film 1500 may include longitudinal slots for facilitating breathing while still making the posterior tongue thicker. In an alternative embodiment, a tissue dressing infused with lidocaine or other anesthetic may be applied to a surgical site after a traditional sleep apnea surgical procedure. As with other embodiments, the materials, structure, and texture of support film 1500 can be chose to meet the performance goals of these embodiments.

In other embodiments, a tissue dressing may be used for other purposes. For example, a tissue dressing may be used as a plug, such as to stop CSF leaks after skull base surgery, as mentioned above. A dressing may also be used to cover the site of a puncture through the canine fossa into a maxillary sinus. Such punctures are sometimes formed, for example, to access a maxillary sinus to perform sinus surgery. A tissue dressing may be used in oral surgery or tooth extractions to help stop or minimize bleeding.

In yet another embodiment, a mucosal tissue dressing film may be used as an iontophoresis pad for delivering drug to or through a tissue. Iontophoresis generally involves driving a substance across a tissue by applying electrical energy to the substance and driving the substance toward a receiver of the electrical energy. In one embodiment, the tissue film may be used in this capacity for driving substance across any tissue membrane in the ear, nose, throat or mouth.

Example 1

In this example, dressings were made from films composed of modified cellulose.

Method—all the raw materials are prepared into solutions in certain concentrations respectively; then the solutions are coated on a PTFE sheet individually or in mixture with single or double layers to make different films.

1. Raw Materials

Polypropylene glycol (PPG), Alfa Aesar Cat#40811, Lot#K28Q011, used as received.

DI water was prepared on site by DI water generation system.

The following raw materials are prepared into solutions for use:

Ethanol, Aldrich Cat#493546-1L, Lot#06862EH
Ethyl cellulose (EC), Spectrum Cat# ET110, Lot# UT0371
Methyl cellulose (MC), Aldrich Cat# M0555-100G, Lot#037K00611
Hydroxypropyl methyl cellulose (HPMC), Aldrich Cat# H3785-100G, Lot#086K0115.

2. Solution Preparation

Ethyl Cellulose Solution Preparation

Composition: 20 wt % ethyl cellulose (EC) in USP grade ethanol.

Example: 37.5 g EC in 150 g Ethanol.

Preparation: weigh desired amounts of EC and ethanol, mix them together in a storage bottle, stir the solution on vortex mixer, and leave it for 2-3 days before use.

Methyl Cellulose Solution Preparation

Composition: 5 wt % methyl cellulose (MC) in USP ethanol/DI water (1/1 wt).

Example: 32 g MC in 300 g ethanol/300 g DI water.

Preparation: weigh desired amounts of MC, ethanol, and DI water, mix them together in a storage bottle, then add DI water, stir the solution on vortex mixer, and leave it for 2-3 days before use.

Hydroxypropyl Methyl Cellulose Solution Preparation

Composition: 7 wt % hydroxypropyl methyl cellulose (HPMC) in USP ethanol/DI water (1/1 wt).

Example: 28.6 g HPMC in 190 g ethanol/190 g DI water.

Preparation: weigh desired amounts of HPMC, ethanol, and DI water; transfer weighed HPMC into a storage bottle, transfer ethanol into the bottle and mix the solution to let the HPMC powder uniformly disperse in ethanol; add weighed DI water into the bottle while stirring until finish; stir the solution, and leave it for 2-3 days before use.

3. Equipment or Tools

Vacuum oven: Lab-Line Instruments, model#3608, used for film drying

Gel dryer: Bio-Rad, model#583, used for film drying and flattening

Shaker: New Brunswick Scientific, model# Classic C1, used for solution stirring

PTFE sheet: 1.0 mm thick, in sizes: 6×6, 6×12, 6×18 cm$^2$, used as a film coating substrate PTFE coated tray: bottom size: 10×20 cm$^2$, used as a film coating substrate Stainless steel spatulas: used for film coating 500 ml wide mouth reagent bottles: used for solution storage Glass beakers: 250 ml, used for solution mixing for film coating Disposable pipettes: used to transfer PPG liquid Aluminum foil: used cover the coated films.

4. Film Preparation

The thickness of the prepared film primarily depends on several factors, e.g., material bulk density, substrate surface area, quantity of material solution coated on the substrate surface. The following formula can be used to estimate the thickness of the prepared dry film:

$$q = (W \times C)/(D \times A)$$

where, W is the quantity of material solution used for casting a film; C refers to the solid content of the material solution in weight percent; D is material bulk density; and A stands for the area of the substrate surface. PTFE and PE polymer sheets or dishes, or PTFE coated tray, can be used as substrate surfaces for film casting.

1) Single-Layer Film Preparation

General Procedures:

a) Based on the above formula, a determined quantity of material solution (or solutions, if a solution mixture is used) is weighed (or then mixed).

b) Coat the weighed solution (or mixed solutions) on the surface of a given substrate sheet or dish.

c) Put the coated substrate sheet or dish in chemical hood or vacuum oven to dry slowly.

d) After the film is fully dried, peel it off from the substrate surface, weigh it and measure its thickness.

Example of Single-Layer Film:

HPMC single-layer film preparation on a 6×18 cm2 PTFE sheet.

Targeted thickness: 0.3 mm, dry film density: 0.85 g/cm$^3$

Weighing the PTFE sheet (24.16 g), and weighing 39.36 g 7 wt % HPMC solution on the PTFE sheet, uniformly flattening the viscous HPMC solution on the whole sheet, putting it in a tray with foil cover, and then place the tray in vacuum oven to dry slowly (about 65 hrs).

Weigh and measure the thickness of the dried film.

2) Double-Layer Film Preparation

General Procedures:

a) The protective layer is coated first according to the procedures of 1a, 1b, and 1c.

b) After the protective layer is partially dried (Dry for 1~2 hours depending on the expected film thickness. The extent of dryness can be observed as loss of the wet area of the coated surface.). Start to coat the top layer.

c) The top layer is coated according to the procedures of 1a, 1b, and 1c.

d) After the double-layer film is fully dried, peel it off from the substrate surface, weigh it and measure its thickness.

Example of Double Layer Film

HPMC double-layer film preparation on a 6×18 cm2 PTFE sheet.

Film structure: EC:MC:PPG/HPMC:PPG=4:4:2/8:2 (wt)

a) Protective Layer

Targeted thickness: 0.1 mm, dry layer density: 0.67 g/cm$^3$,

Weigh the PTFE sheet (24.58 g).

Weigh and zero the empty beaker. Weigh 1.86 g 20 wt % EC solution, 7.5 g 5 wt % MC solution, and 0.186 g PPG in the beaker, mixing the solutions into a uniform slurry (7.11 g of this mixture will be used to coat a layer on 6×18 cm2 PTFE sheet, assuming no solvent evaporation). Weigh the mixture again to calculate the solvent weight loss, then transfer the mixture in an equivalent weight to the theoretical amount of 7.11 g to the PTFE sheet. Uniformly flatten the mixture on the whole sheet, and then put it in chemical hood for solvent evaporation.

b) Adhesive Layer

Targeted thickness: 0.2 mm, dry layer density: 0.85 g/cm$^3$.

Weigh the protective layer coated sheet and monitor the remaining weight with the time.

Weigh and zero the empty beaker. Weigh 30 g 7 wt % HPMC solution, and 0.502 g PPG in the beaker, mixing the solutions into a uniform slurry (20.92 g of this mixture will be used to coat a layer on the above coated protective layer, assuming no solvent evaporation); when the remaining weight percentage of the coated protective layer is around 25 wt %, weigh the mixture again to calculate the solvent weight loss, then transfer the mixture in an equivalent weight to the theoretical amount of 20.92 g onto the protective layer. Uniformly flatten the mixture on the whole layer, and then put it in hood, vacuum oven, and gel dryer, for to dry slowly, e.g, Hood—30 min, 50° C. oven—3 hr, 35° C. oven—17 hr, 50° oven—4 hr, 70° C. gel dryer—2 hr.

Weigh and measure the thickness of the dried film. e.g., 2.5 g and 0.31 mm for film CMT1114-1a.

Example of Multilayer Film

MC double-layer film preparation on a 6×18 cm$^2$ PTFE sheet.

Film structure: EC:MC:PPG/MC:PPG=4:4:2/8:2 (wt)

a) Protective Layer

Targeted thickness: 0.1 mm, dry layer density: 0.67 g/cm$^3$,

Weigh PTFE sheet (24.62 g).

Weigh and zero the empty beaker Weigh 1.86 g 20 wt % EC solution, 7.5 g 5 wt % MC solution, and 0.186 g PPG in the beaker, mixing the solutions into a uniform slurry (7.12 g of this mixture will be used to coat a layer on 6×18 cm2 PTFE sheet, assuming no solvent evaporation); Weigh the mixture again to calculate the solvent weight loss, then transfer the mixture in an equivalent weight to the theoretical amount of 7.11 g to the PTFE sheet. Uniformly flatten the mixture on the whole sheet, and then put it in chemical hood for solvent evaporation.

b) Adhesive Layer

Targeted thickness: 0.2 mm, dry layer density: 0.85 g/cm3.

Weigh the protective layer coated sheet and monitor the remaining weight with the time.

Weigh and zero the empty beaker. Weigh 40 g 5 wt % MC solution, and 0.5 g PPG in the beaker, mixing the solutions into a uniform slurry (29.39 g of this mixture will be used to coat a layer on the above coated protective layer, assuming no solvent evaporation); when the remaining weight percentage of the coated protective layer is around 25 wt %, weigh the mixture again to calculate the solvent weight loss, then transfer the mixture in an equivalent weight to the theoretical amount of 29.39 g onto the protective layer. Uniformly flatten the mixture on the whole layer, and then put it in hood, vacuum oven, and gel dryer, for to dry slowly, e.g, 35° C. oven—15 hr, 50° C. oven—8 hr, 35° C. oven—15 hr, 70° C. gel dryer—2 hr.

Weigh and measure the thickness of the dried film, e.g., 2.22 g and 0.29 mm for film CMT1114-4.

5. Film Compositions

|  | Adhesive Layer HPMC | | Adhesive Layer MC | | Protective Layer | | |
|---|---|---|---|---|---|---|---|
|  | Wt of HPMC (g) | Wt of PPG (g) | Wt of MC (g) | Wt of PPG (g) | Wt of EC (g) | Wt of MC (g) | Wt of PPG (g) |
| HPMC Single-Layer Film 6 × 18 cm$^2$ | 2.76 | N/A | N/A | N/A | N/A | N/A | N/A |
| HPMC Double-Layer Film 6 × 18 cm$^2$ | 1.44 | 0.36 | N/A | N/A | 0.28 | 0.28 | 0.14 |
| MC Double-Layer Film 6 × 18 cm$^2$ | N/A | N/A | 1.45 | 0.36 | 0.28 | 0.28 | 0.14 |

6. Discussions

1) Solution Preparation

In preparation of material solutions, the solutions should be shelved for several days to ensure the solutions become homogenous. If the solutions are not homogeneous, the films made from the solutions will be uneven.

2) Solution Storage and Use

The prepared solutions should be weighed and then well sealed to prevent solvent evaporation. Solvent loss via evaporation can be calculated by weighing the solutions after and before use. If any solvent loss occurs, the solvent should be added to the recipe amount. Solvent loss will cause the solution concentration to change making it difficult to control the film thickness.

3) Protective Layer Drying

Protective layer drying is critical to the adhesive layer coating. If the adhesive layer is coated onto a protective layer that has not dried sufficiently, the two layers may be mixed together, thus the double-layer structure may be destroyed. If the adhesive layer is coated onto a protective layer that is dried too completely, the two layers may be easily separated following application.

A factor can be used to estimate the drying extent, that is, the remaining weight percentage of the coated protective layer, which can be calculated by using the following equation:

$$\text{Remaining weight \%} = (W_t - W_s)/(W_i - W_s) \times 100\%$$

where, $W_t$ is the weight of the coated PTFE sheet after drying for a certain time, $W_s$ is the weight of the uncoated PTFE sheet, and $W_i$ is the initial weight of the coated PTFE sheet. When the remaining weight % falls in the range of 15-30% or the best level of 25%, the adhesive layer should be coated onto the protective layer immediately.

4) Adhesive Layer Drying

Several problems may be encountered during the drying course of the adhesive layer (including single layer film), especially when producing a thick layer. Generally, cracks, shrinkage, waves, wrinkles, bubbles, and uneven thickness, might be seen if the drying conditions are not carefully controlled.

Basically, a slow drying process and particularly a slow solvent evaporation on the film surface may significantly avoid the aforementioned problems and improve the film drying quality. Meanwhile, wavy shape can be eliminated by using a gel dryer when the film is nearly fully dried.

Example 2

Film Adhesion Strength Test

For the evaluation of the adhesion strength of oral wound dressing film samples, An apparatus was set up, which can be used to evaluate the film samples for their adhesion performances. Two types of adhesion strength, i.e., lift-off strength and peel-off strength, can be measured through the use of the apparatus.

1. Lift-Off Adhesion Strength Test Setup and Procedures

Figure 16:
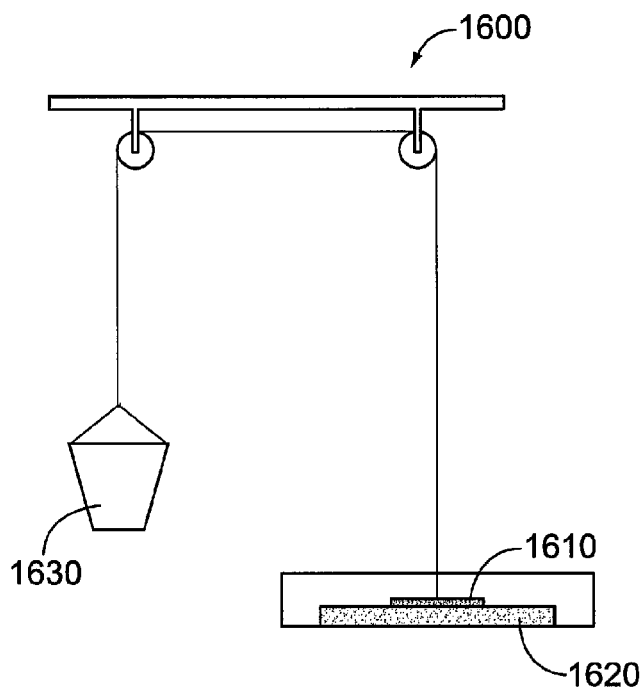
FIG. 16 illustrates a lift-off adhesion test method.

By measuring the vertical detaching force and time, the lift-off adhesion strength of the film adhering to fresh pork steak can be tested. The test apparatus 1600 is set up as shown in FIG. 16. Tests are performed at room temperature, 23 deg. C. The procedures are described below:

1) Cut a sample film 1610 in a certain size, e.g., 15×15 mm$^2$;

2) Use superglue to fix a fresh, boneless pork steak 1620 to the bottom of a dish;

3) Use Scotch tape to fix the string at the center of sample (for single-layer film) or sample protective layer (for double-layer film); a small amount of super glue can be used to further secure the tape to the sample as long as no super glue penetrates the sample to affect its adhesive properties.

4) Put the sample adhesive layer on the fresh pork steak 1620 surface, and press the film to let it adhere to the steak surface and leave it for 5 minutes (curing time);

6) After 5 minutes start the timer and immediately add water into the loading cup 1630 drop-by-drop smoothly until either the film is lifted off or the cup is filled fully;

7) note the time when the film has lifted off the steak.

8) If the film is lifted off, weigh the weight of the loading cup 1630 with water and note the weight as the lift-off adhesion strength of the sample.

9) If the loading cup 1630 is added to full level and the film still adheres to the steak, then record the lift-off time. So the lift-off adhesion strength should be noted as the adhering time under the full loading.

2. Peel-Off Adhesion Strength Test Setup and Procedures

Figure 17:
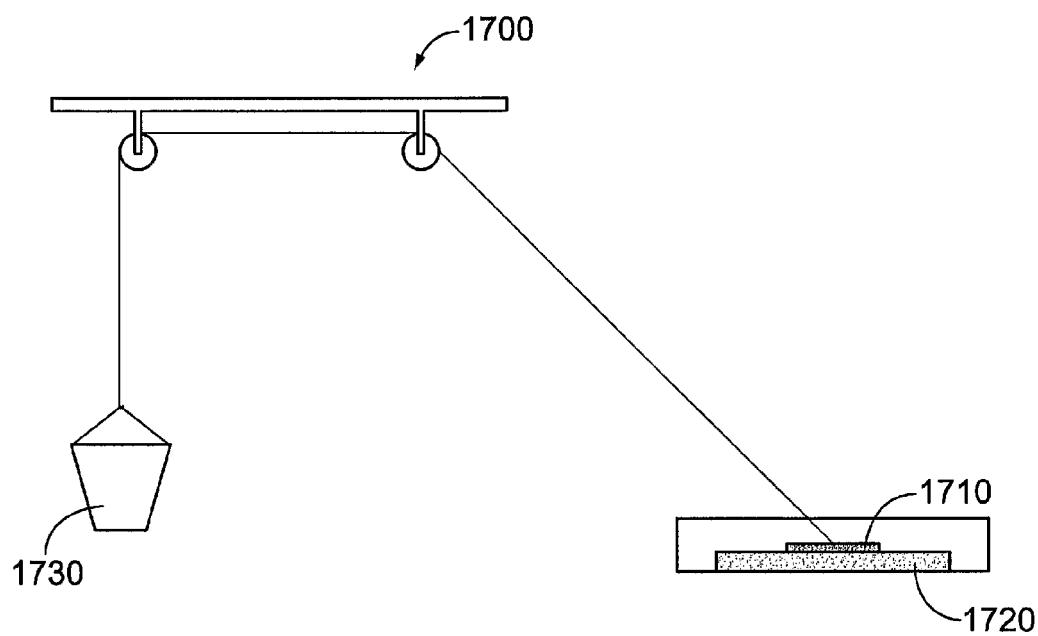
FIG. 17 illustrates a peel-off adhesion test method.

By measuring the angle (45 degree) detaching force and time, the peel-off adhesion strength of the film adhering to fresh pork steak can be tested. The test apparatus 1700 is set up as shown in FIG. 17. Tests are performed at room temperature, 23 deg. C. The procedures are described below:

1) Cut a sample film 1710 in a certain size, e.g., 15×15 mm$^2$;

2) Use superglue to fix a fresh pork steak 1720 on the bottom of a dish;

3) Use Scotch tape to fix the string at the edge of sample (for single-layer film) or sample protective layer (for double-layer film); a small amount of super glue can be used to further secure the tape to the sample as long as no super glue penetrates the sample to affect its adhesive properties.

4) Put the sample adhesive layer on the fresh pork steak 1720 surface, and press the film to let it adhere to the steak surface and leave it for 5 minutes (curing time);

6) After 5 minutes start the timer and immediately add water into the loading cup 1730 drop-by-drop smoothly until either the film is peeled off or the cup is filled fully;

7) Stop the timer and note the time when the film is peeled off.

8) After the film is peeled off, weigh the weight of the loading cup 1730 with water and note the weight as the peel-off adhesion strength of the sample.

9) If the loading cup 1730 is added to full level and the film still adheres to the steak, then record the peel-off time. So the peel-off adhesion strength should be noted as the adhering time under the full loading.

Example 3

In this example, films were tested for properties desirable in a dressing. The set time, or the time it takes for a hydrogel to form, was measured for each of the adhesion films. Carboxymethyl cellulose performed better than hydoxypropyl methyl cellulose, which in turn performed better than methyl cellulose. All adhesion films and the barrier film displayed good flexibility and lack of swelling. All adhesion films and the barrier film remained intact in artificial saliva. In degradation testing, after 5 days the carboxymethyl cellulose film was 70% degraded, the hydoxypropyl methyl cellulose film was 40% degraded, the methyl cellulose film was 25% degraded, and the barrier films was 15% degraded. All degradation values are given by weight.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of treating a tonsil removal site after a tonsillectomy procedure, the method comprising:
   (a) applying a dressing over the tonsil removal site, wherein one side of the dressing is adapted to adhere to a surgical site and an opposite side of the dressing is adapted to provide abrasion resistance, the opposite side of the dressing embodying material characteristics distinct from the one side of the dressing adapted to adhere, and further wherein the dressing includes pores;
   (b) polymerizing the dressing, wherein the act of polymerizing the dressing occurs after the dressing has been positioned to cover at least a portion of the tonsil removal site; and
   (c) releasing a drug from the dressing.

2. The method of claim 1, wherein at least a portion of the dressing is configured to dissolve over time.

3. The method of claim 1, wherein the drug is released over a course of days.

4. The method of claim 1, wherein the drug is released over a course of weeks.

5. The method of claim 1, wherein the drug is configured to reduce pain.

6. The method of claim 1, wherein the drug is configured to promote healing.

7. The method of claim 1, wherein the dressing is chemically treated such that peptides or proteins are bonded to surfaces thereof.

8. The method of claim 1, wherein the dressing has been treated by bombarding with plasma or ions.

9. The method of claim 1, wherein the dressing includes dimples.

10. The method of claim 9, wherein the dimples or pores are formed by molding, machining, chemically etching, or ablating a surface of the dressing.

11. The method of claim 1, wherein the dressing includes a porous layer formed by using gas-evolution foaming techniques and incorporating and subsequently dissolving prosigens.

12. The method of claim 1, wherein the dressing includes a fibrous surface formed by weaving or felting techniques.

13. The method of claim 1, wherein the dressing comprises an elastic hydrated film.

14. The method of claim 1, wherein the dressing comprises an adhesive layer and a removable backing, the method further comprises removing the backing before applying the dressing over the tonsil removal site.

15. The method of claim 1, wherein the side of the dressing adapted to adhere to a surgical site is textured to facilitate adhesion to tissue.

16. The method of claim 1, wherein the dressing comprises an outer rim and a concave central region, wherein the concave central region is configured to conform to a tonsil bed at the tonsil removal site.

17. A method of treating a tonsil removal site after a tonsillectomy procedure, the method comprising:
    (a) positioning a dressing proximate to the tonsil removal site, wherein one side of the dressing is adapted to adhere to a surgical site and an opposite side of the dressing is adapted to provide abrasion resistance, the opposite side of the dressing embodying material characteristics distinct from the one side of the dressing adapted to adhere, and further wherein the dressing includes pores;
    (b) applying the dressing, wherein the act of applying the dressing comprises applying the dressing in a liquid form to the tonsil removal site; and
    (c) releasing a drug from the dressing.

18. The method of claim 17, wherein the act of applying the dressing in a liquid form to the tonsil removal site comprises painting the dressing on the tonsil removal site.

19. The method of claim 17, wherein the act of applying the dressing in a liquid form to the tonsil removal site comprises spraying the dressing on the tonsil removal site.

* * * * *